(12) United States Patent
Pond

(10) Patent No.: US 6,390,815 B1
(45) Date of Patent: May 21, 2002

(54) MULTIPLE SOLUTION DENTAL IRRIGATOR

(76) Inventor: Gary J. Pond, 2816 N. Main St., Racine, WI (US) 53402

(*) Notice: Subject to any disclaimer, the term of this patent is extended or adjusted under 35 U.S.C. 154(b) by 0 days.

(21) Appl. No.: 09/538,255

(22) Filed: Mar. 30, 2000

Related U.S. Application Data

(63) Continuation-in-part of application No. 09/468,524, filed on Dec. 21, 1999.

(51) Int. Cl.$^7$ .............................................. A61C 17/00
(52) U.S. Cl. ........................................ 433/80; 433/100
(58) Field of Search ............................ 433/80, 84, 85, 433/99, 100, 32, 98, 27

(56) References Cited

U.S. PATENT DOCUMENTS

| | | | |
|---|---|---|---|
| 611,136 A | 9/1898 | Mason | 606/538 |
| 1,672,114 A | 6/1928 | Crow | 604/249 |
| RE21,187 E | 8/1939 | Hooper | 604/249 |
| 2,214,230 A | 9/1940 | Freeburg | |
| 2,557,222 A | 6/1951 | Goode | |
| 2,711,586 A | 6/1955 | Groves | 433/95 |
| 2,756,740 A | 7/1956 | Deane | |
| 2,812,765 A | 11/1957 | Tofflemire | |
| 2,929,510 A | 3/1960 | Penn | |
| 2,985,285 A | 5/1961 | Riddle | |
| 3,164,153 A | 1/1965 | Zorzi | |
| 3,208,145 A | 9/1965 | Turner | |
| 3,593,423 A | 7/1971 | Jones et al. | |
| 3,624,907 A | 12/1971 | Brass et al. | |
| 3,640,304 A | 2/1972 | Fox et al. | 433/80 |
| 3,645,497 A | 2/1972 | Nyboer | 251/148 |
| 3,718,973 A * | 3/1973 | Slater et al. | 433/98 |
| 3,727,310 A | 4/1973 | Baker | |
| 3,757,421 A * | 9/1973 | Kraft | 433/98 |
| 3,971,375 A * | 7/1976 | Hill | 433/98 |
| 4,106,198 A | 8/1978 | Childress | |
| 4,215,476 A | 8/1980 | Armstrong | 433/80 |
| 4,227,878 A | 10/1980 | Lohn | 433/80 |
| 4,253,831 A | 3/1981 | Eaton, II | 433/9 |
| 4,340,365 A | 7/1982 | Pisanu | 433/80 |
| 4,353,694 A | 10/1982 | Pelerin | 433/77 |
| 4,397,640 A | 8/1983 | Haug et al. | 604/33 |
| 4,526,573 A | 7/1985 | Lester et al. | 604/33 |
| 4,552,531 A | 11/1985 | Martin | 433/147 |
| 4,578,055 A | 3/1986 | Fischer | 604/2 |
| 4,680,026 A | 7/1987 | Weightman et al. | 604/33 |
| D302,586 S | 8/1989 | Zogg et al. | D24/15 |
| 4,872,837 A | 10/1989 | Issalene et al. | 433/29 |
| 5,044,953 A | 9/1991 | Sullivan | 433/92 |
| 5,052,927 A | 10/1991 | Discko, Jr. | 433/90 |
| 5,061,180 A | 10/1991 | Wiele | 433/91 |
| 5,087,198 A | 2/1992 | Castellini | 433/80 |
| 5,171,146 A | 12/1992 | Guerci | 433/81 |
| 5,199,604 A * | 4/1993 | Palmer et al. | 433/80 |
| 5,204,004 A | 4/1993 | Johnston et al. | 210/651 |
| 5,230,704 A | 7/1993 | Moberg et al. | 604/34 |
| 5,236,356 A | 8/1993 | Davis et al. | 433/80 |
| 5,289,919 A | 3/1994 | Fischer | 206/571 |

(List continued on next page.)

OTHER PUBLICATIONS

Kent Dental Spring / Summer 1984 Product Catalog—p. 153–154.

*Primary Examiner*—Cary E. O'Connor
(74) *Attorney, Agent, or Firm*—Ryan Kromholz & Manion, S.C.

(57) ABSTRACT

A fluid dispensing assembly that may be used to supply fluid for use in dental instrumentation including irrigation, application, and aeration for treating a patient's mouth. The fluid dispensing assembly includes a fluid supply system that conveys fluid by pressurized air, and also includes a handpiece to allow flow between the fluid supply system and the patient's mouth. The fluid dispensing assembly further includes a separate handpiece for the delivery of only air into a patient's mouth.

29 Claims, 15 Drawing Sheets

U.S. PATENT DOCUMENTS

| | | | |
|---|---|---|---|
| 5,378,149 A | 1/1995 | Stropko | 433/80 |
| 5,378,150 A | 1/1995 | Harrel | 433/91 |
| 5,419,772 A | 5/1995 | Teitz et al. | 604/141 |
| 5,468,148 A | 11/1995 | Ricks | 433/80 |
| 5,474,450 A | 12/1995 | Chronister | 433/80 |
| 5,526,841 A | 6/1996 | Detsch et al. | 137/15 |
| 5,554,026 A | 9/1996 | Van Hale | 433/82 |
| 5,556,279 A | 9/1996 | Wolf et al. | 433/82 |
| 5,593,304 A | 1/1997 | Ram | 433/82 |
| 5,658,144 A | 8/1997 | Tinder et al. | 433/80 |
| 5,716,210 A | 2/1998 | Novak | 433/82 |
| 5,772,433 A | 6/1998 | Esrock | 433/80 |
| 5,837,204 A | 11/1998 | Prevost et al. | 433/80 |
| 5,876,201 A | 3/1999 | Wilson et al. | 433/80 |
| 5,899,692 A | 5/1999 | Davis et al. | 433/80 |
| 5,927,977 A * | 7/1999 | Sale et al. | 433/80 |
| 5,947,729 A * | 9/1999 | Bell | 433/98 |

* cited by examiner

MULTIPLE SOLUTION DENTAL IRRIGATOR

This application is a continuation-in-part of U.S. application Ser. No. 09/468,524 filed Dec. 21, 1999, pending.

BACKGROUND OF THE INVENTION

1. Field of the Invention

This invention relates to systems and methods and methods for systems for providing fluid to a hand tool and associated supply lines.

2. Description of Related Art

As a patient sits in a dental chair in a dentist's office, the dentist or a hygienist ordinarily cleans the patient's teeth with a variety of picks and brushes. Next, the dentist or a hygienist uses a hand held tool to supply rinse water or a variety of other medicament fluids from supply lines to a patient's mouth. Also, during many endodontic procedures, the dentist or dentist's assistant may be required to apply multiple medicaments to the operative site during a single procedure. U.S. patent application Ser. No. 09/468,524, filed on Dec. 21, 1999, commonly assigned to the assignee hereof, discloses a similar design, but it will be appreciated by those skilled in the art that the present invention includes numerous improvements.

A single air supply is commonly utilized in each dental operatory. The air supply pressure in a particular dental office is unique to that office because some dentists may operate more or fewer air operated devices than other dentists operate from a single air supply.

Some dental handpieces are able to supply a plurality of fluids to a patient's mouth. One such example is U.S. Pat. No. 4,215,476 to Armstrong. However, such handpieces often involve complex solenoid valves and more expensive electrical controls to toggle between fluid sources. Further, such handpieces often physically toggle fluid sources at the fluid source, controlled by a toggling at the handpiece. It has been found that toggling fluid sources at the handpiece itself, rather than at the more remote fluid source, requires a much lesser volume of fluid to be purged through the lines after fluid changes. Toggling at the handpiece itself results in less fluid waste, and reduces the risks that fluids may interact within a common fluid line and lead to undesirable chemical reactions.

The temperature of the fluids supplied by handpieces such as in the above-referenced Armstrong patent is generally equal to room temperature. Depending upon the time of year and geographical climate, actual room temperature may vary somewhat and thus affect the temperature of the fluids supplied by such handpieces. It has been found that by heating the fluids supplied by the handpiece, the benefits are two-fold. First, the patient's comfort is increased when the fluids supplied to the patient's mouth have been warmed to a comfortable temperature. Second, the efficacy of many of the fluids is increased when the fluids are heated above ambient temperature.

SUMMARY OF THE INVENTION

To overcome the above-identified concerns, the present invention provides an inexpensive apparatus and method for a fluid supply system that is capable of supplying a selected one of a plurality of fluid sources to a patient's mouth.

The various components may be made using conventional molding and extrusion techniques from inexpensive materials, both relatively rigid and also very flexible when needed or required.

A fluid dispensing assembly for dispensing a plurality of fluids is disclosed, the fluid dispensing assembly comprising a remote touch pad, a handpiece, a fluid discharge tip disposed on the handpiece, a manifold disposed within the handpiece, and a control mechanism disposed on the handpiece. The control mechanism includes a pinch valve for dispensing fluid from the fluid discharge tip. Preferably, both the handpiece and the remote touch pad include a momentary operated switch which actuates a remotely located air valve for selectively pressurizing one of a plurality of reservoirs. Further, the remote touch pad may include a digital or similar visual display. The handpiece manifold comprises a plurality of fluid inlets and a single fluid outlet. The handpiece further comprises a detachable coupling enabling the operator to detach the handpiece from the fluid supply system so that the handpiece may be autoclaved. The fluid dispensing assembly further comprises a fluid supply system, a plurality of fluid outlet lines, the fluid outlet lines preferably surrounding a heating element, and the fluid outlet lines communicatively coupled between the fluid supply system and the fluid inlets.

The fluid supply system comprises a plurality of reservoirs, a volume of fluid contained within each reservoir, and a reservoir head detachably coupled to each reservoir. A source of pressurized air is used to pressurize each reservoir and, in turn, force fluid from each reservoir to the fluid inlet on the handpiece. An air pressure regulator can be used to adjust air pressure, and thus adjust fluid flow from the handpiece. As the fluid is forced from a reservoir, it may be heated by the previously mentioned optional heating element.

The fluid dispensing assembly further comprises a single-fluid dental handpiece for delivering a dedicated fluid, such as air, to a patient's mouth. The single-fluid handpiece may include a control mechanism in the form of a valve for actuating between fluid discharge and no discharge.

Further, the invention comprises a fluid dispensing assembly whereby the dentist can supply pre-selected fluids to irrigate the field of operation within a patient's mouth. In addition, the invention includes a pressurized air supply and a single—fluid handpiece by which the dentist may deliver only a single fluid, such as pressurized dry air, to the patient's mouth.

A method for dispensing a selected fluid from a handpiece is also disclosed, the method comprising attaching a plurality of fluid-containing reservoirs to respective reservoir heads, coupling a plurality of fluid outlet lines between the fluid containing reservoirs and a handpiece, depressing a momentary switch disposed on the handpiece or disposed on a touch pad housing in order to select the desired fluid, the momentary switch being operable to select a particular fluid from among a plurality of fluids, air pressure being supplied to the selected fluid-containing reservoir, the pressurized air forcing the fluid from the selected fluid-containing reservoir through the respective fluid outlet line to the handpiece, and actuating a control mechanism to allow the fluid to pass from the selected fluid outlet line through the handpiece and ultimately the tip.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

Accordingly, it is an object of the present invention to provide a system that minimizes or substantially eliminates the corrosive effects of fluids, such as sodium hypochlorite, on the components of the fluid supply system.

It is another object of the present invention to provide a system including check valve means for minimizing cross contamination of fluids.

It is a further object of the present invention to provide means for minimizing cross-contamination of fluids in the event that the fluid dispensing assembly is jostled or tipped from its upright position.

It is yet another object of the present invention to provide fluid heating means for both patient comfort and for increasing the efficacy of fluids delivered by the fluid supply system.

It is yet a further object of the present invention to provide a separate handpiece for the delivery of a single fluid, such as dry air, to the patient's mouth.

These and other objects will become apparent in the following detailed description and the drawings take in conjunction therewith.

DETAILED DESCRIPTION

Although the disclosure hereof is detailed and exact to enable those skilled in the art to practice the invention, the physical embodiments herein disclosed merely exemplify the invention which may be embodied in other specific structure. While the preferred embodiment has been described, the details may be changed without departing from the invention, which is defined by the claims.

It is to be noted that like elements of the drawings are designated by like reference numbering.

The term "fluid," as used herein, shall be defined as a gas including air, a liquid, a substance which flows, or a substance which differs from a solid in that it can offer no permanent resistance to change of shape. It shall further include mixtures of gases, mixtures of liquids, and mixtures of gases and liquids.

The invention includes a housing, at least one fluid reservoir, a fluid reservoir manifold, at least one handpiece, and a fluid pressurizing mechanism. The fluid pressurizing mechanism in one embodiment comprises at least one pressure regulator, at least one air valve, and a momentary switching means to pressurize at least one selected fluid reservoir. The fluid pressurizing mechanism in the preferred embodiment comprises at least one pressure regulator, a plurality of air valves, each air valve being in communication with a respective fluid reservoir, and a momentary switching means to control each air valve.

Figure 1:
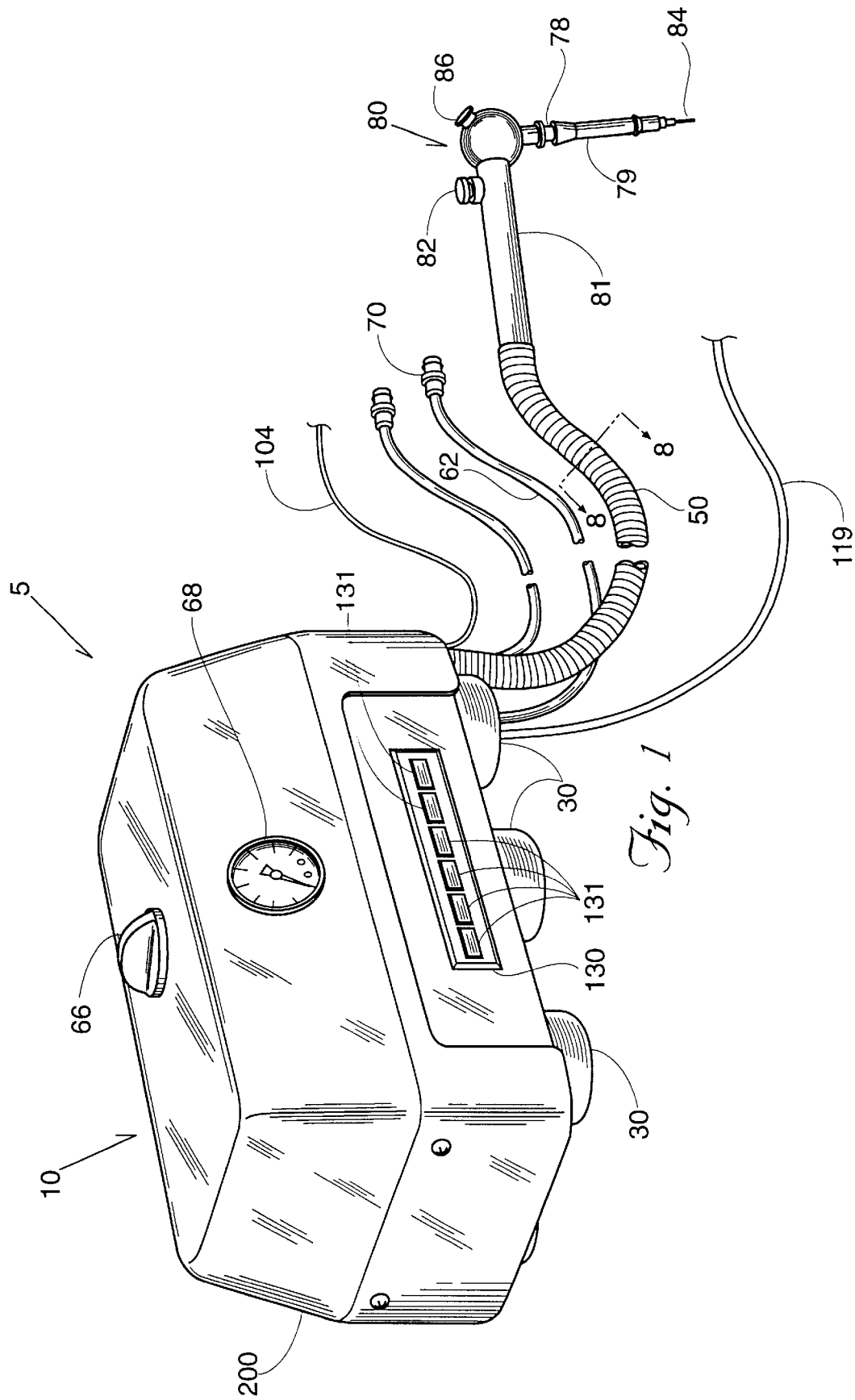
FIG. 1 is a partial perspective view of a fluid dispensing assembly.
Figure 2:
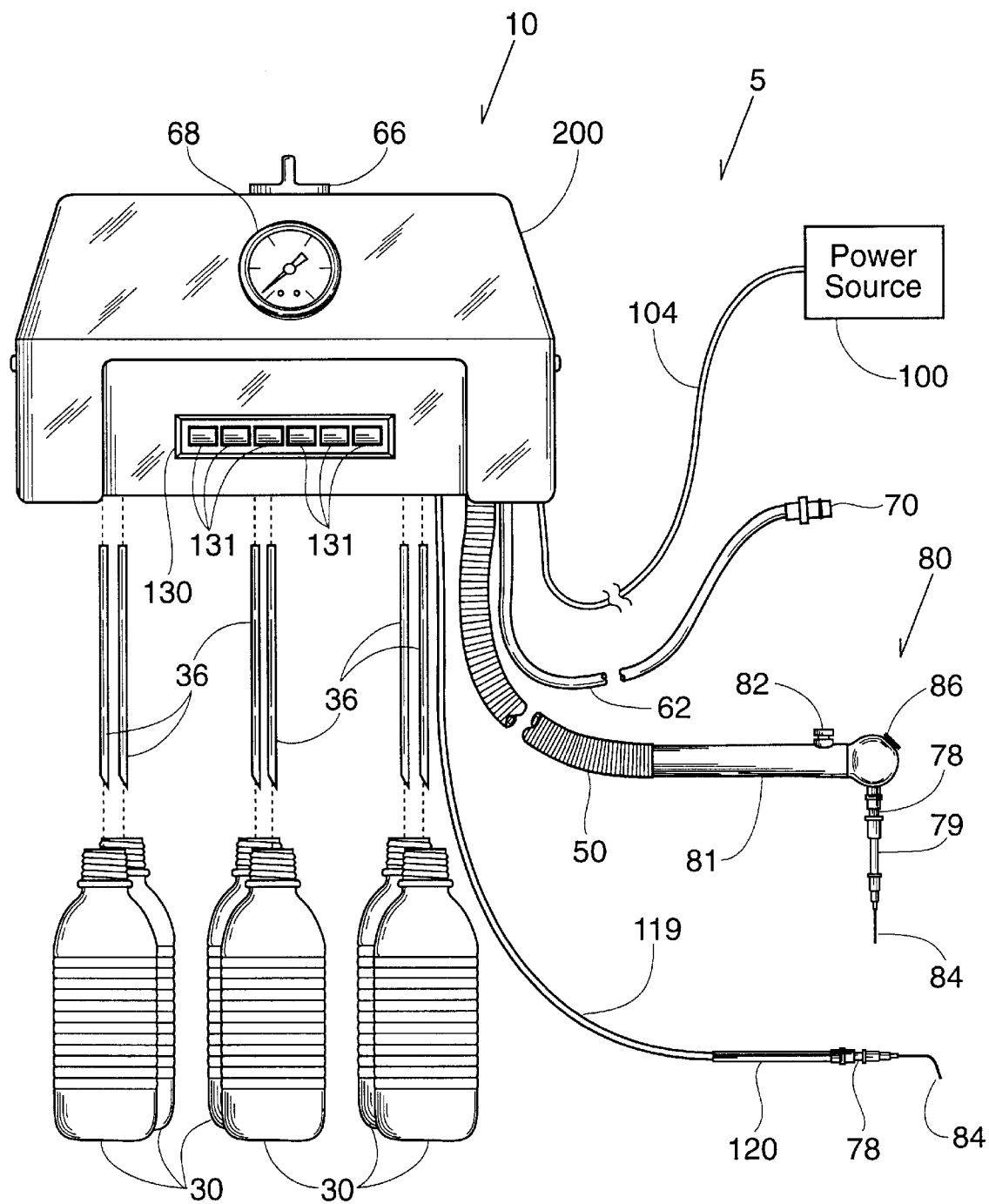
FIG. 2 is a front elevational view of the fluid dispensing assembly of FIG. 1, with certain of the components being shown in exploded relationship.

In one embodiment of the present invention, reference is made to the views of FIGS. 1–8, inclusive. Referring in particular to FIGS. 1 and 2, there is shown a fluid dispensing assembly, indicated generally by the reference numeral 5, capable of supplying irrigation from a fluid supply system, indicated generally by the reference numeral 10 to a dental handpiece 80. Delivery of dry air for aeration purposes or another fluid is preferably supplied from a supply line 119 to a single—fluid dental handpiece 120.

Figure 3:
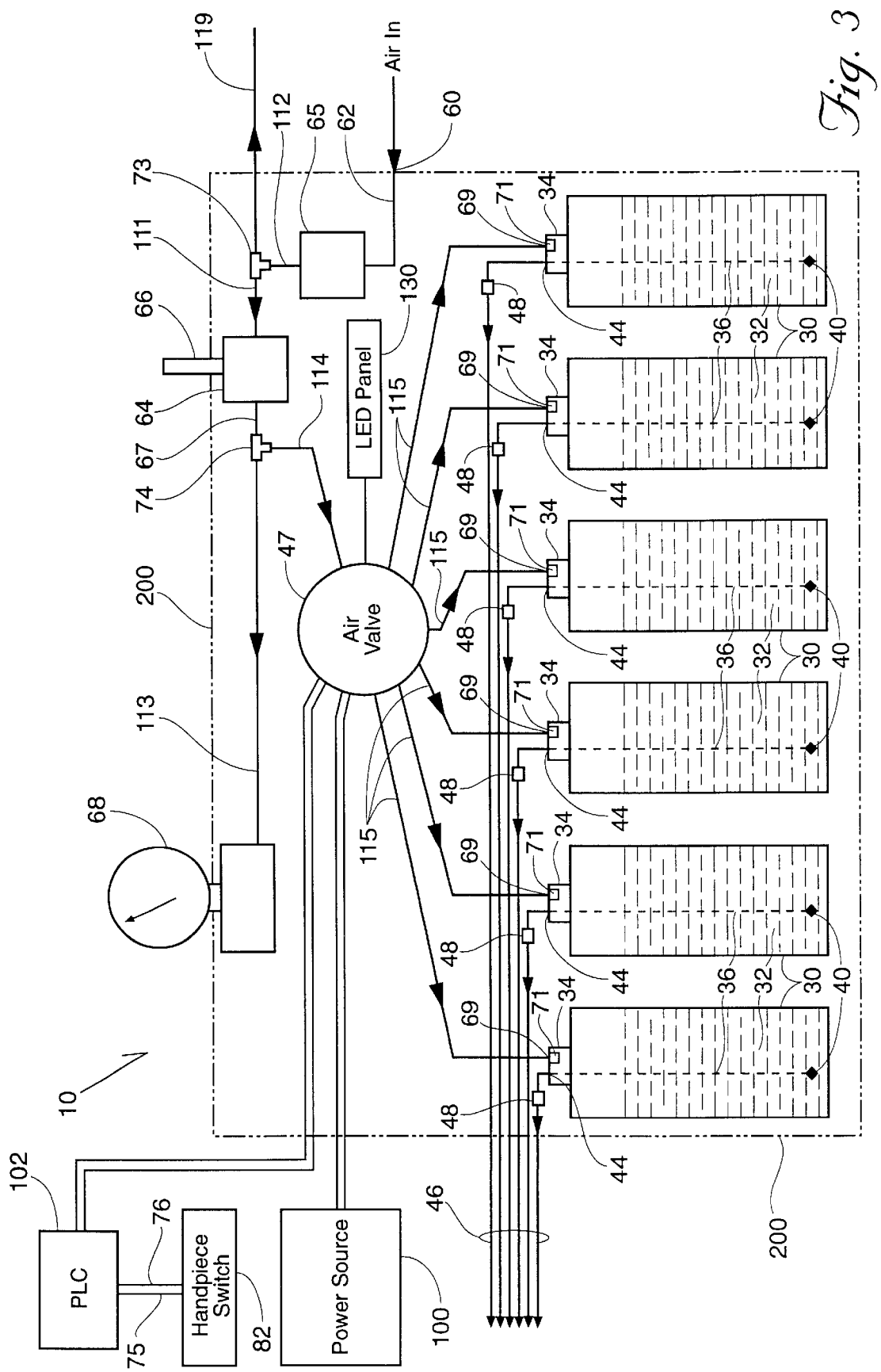
FIG. 3 is a schematic view of a fluid supply system having application in the fluid dispensing assembly of FIGS. 1 and 2.
Figure 4:
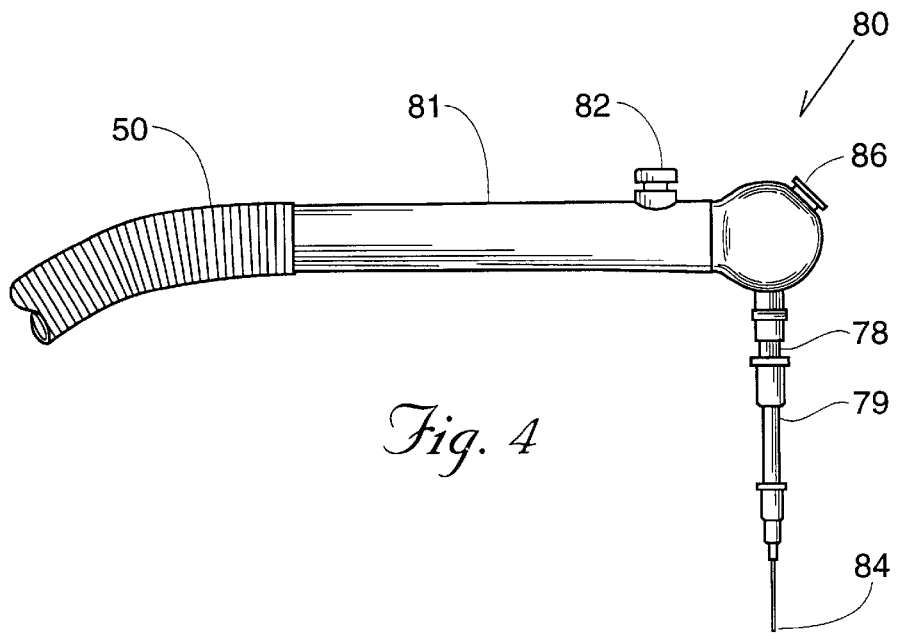
FIG. 4 is a fragmentary, side elevational view of a handpiece used with the fluid dispensing assembly.
Figure 5:
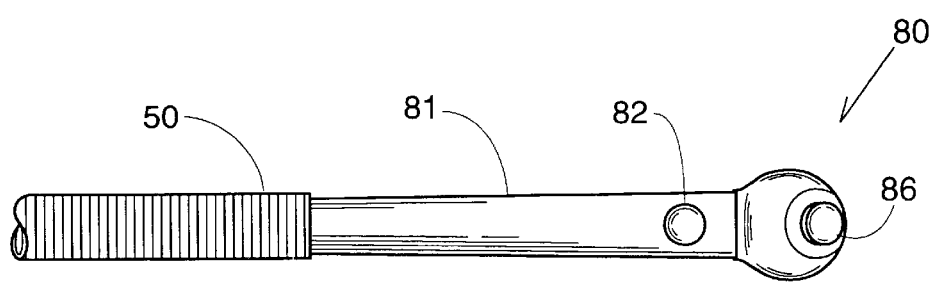
FIG. 5 is a fragmentary, top elevational view of the handpiece used with the fluid dispensing assembly.
Figure 6:
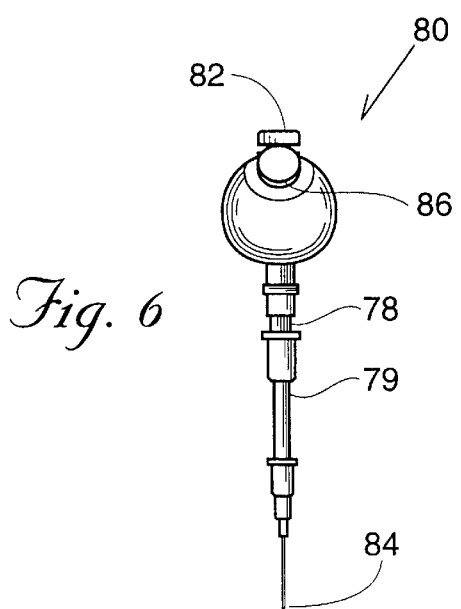
FIG. 6 is a front elevational view of the handpiece of FIGS. 4 and 5.

The fluid dispensing assembly 5 includes at least one reservoir 30 capable of containing fluid 32 (see FIG. 3). The reservoir 30 is carried by a housing 200. While it is apparent that any number of reservoirs could be utilized, the preferred embodiment has six. The reservoir 30 can come in many forms, including, for example, a bottle, a canister, a dual-compartment bottle or canister; and can range greatly in size. Preferably, however, the reservoir 30 is an inexpensive clear plastic bottle with an engageable neck 31, similar to a common water bottle with the cap removed. Reservoirs of this type are readily available from a variety of sources and manufacturers, and are most commonly available in a 10–20 fluid ounce capacity size. The clear bottle allows for a determination of the amount of fluid 32 remaining in the reservoir 30, and a reservoir of this type is capable of withstanding internal pressure, though typically the resistance to pressure for this type of reservoir is limited to approximately 50 pounds per square inch (psi). Although a stronger reservoir is capable of use with the fluid supply system, such as a high density polyethylene reservoir, the polyethylene terephthalate elastomer (PETE) construction common to plastic soda and water bottles provides sufficient rigidity, is easily available, and is inexpensive.

Referring now to FIG. 3, the reservoir 30 is detachably coupled to a reservoir head 34 (hidden from view in FIG. 2). The reservoir head 34 is designed to provide the reservoir 30 with an air-tight seal capable of containing pressures up to 50 psi, but higher pressures are capable with different reservoir embodiments. The detachable coupling may be provided by a threaded neck 31 on the reservoir 30 and a female thread on the reservoir head 34. However, it is to be understood that a variety of means for removably coupling each reservoir to the reservoir head may be employed. The detachable coupling allows for quick and simple reservoir changes, should refills or different fluids be desired for use with the fluid dispensing assembly 5.

The reservoir head 34 has two fluid passageways or two communicative conduits 44 and 69 indicated schematically on FIG. 3, between the reservoir 30 and the remainder of the fluid dispensing assembly 5 and fluid supply system 10. The first communicative conduit provides a pathway to the interior of the reservoir 30 for pressurized air through an air inlet fitting 69. The second communicative conduit is a fluid outlet fitting 44, providing a fluid passage for fluid to leave the reservoir 30.

It is conventional to supply sodium hypochlorite during certain dental procedures to either irrigate, debride and disinfect the mouth of a patient, or to destroy bacteria present in the dental unit water line. The components of the fluid supply system 10 that come into contact with the sodium hypochlorite are preferably constructed of material capable of withstanding the corrosive effects of the sodium hypochlorite. These components, as shown in FIGS. 1–7, inclusive, include a check valve 48, an air valve 47, a fluid draw line 36, a fluid outlet line 46, the fluid outlet fitting 44, the reservoir 30, the reservoir head 34, and the handpiece 80, and are preferably constructed of sodium hypochlorite resistant material. Because sodium hypochlorite is particularly corrosive with respect to metal, non-metal components are preferred. Plastic is a preferred construction material because of its resistance to sodium hypochlorite corrosion. The fluid outlet lines 46 preferably have an inner layer and an outer layer, the inner layer preferably being constructed of polyethylene (PE) and the outer layer preferably being constructed of polyvinyl chloride (PVC).

Dental offices are often unique with respect to the air pressure in the air system. Dental offices operate at higher or lower pressures based on operator preference, the output of the air compressor, the number of components in the office using air, and the number of components in use at any one time. For this reason, the fluid supply system 10 is supplied with an adjustable air pressure regulator 64 and a fixed air pressure regulator 65. Adjustable air pressure regulator 64 is coupled with an air supply line 62 and the air valve 47 between an air inlet 60 and the reservoir 30, as is best shown in FIG. 3. This arrangement avoids erratic and uncontrollable fluid flow from the fluid supply system 10 and ultimately the handpiece. One air pressure regulator that performs suitably is a CLIPPARD MAR-1, 0–27 psi air pressure regulator. Most dentists prefer a setting of approximately 5–10 psi. Preferably, pressure in the fixed air pressure regulator 65 is fixed at 20 psi. Preferably, pressure in the adjustable air pressure regulator 64 is adjustable by operation of an air pressure regulator adjuster 66, according to the operator's preference, to an air pressure from 5 psi to 10 psi.

The operator of the fluid supply system 10 thus has the capability to alter the air pressure to provide a consistent output of fluid.

As previously stated and as shown in FIGS. 1 and 2, the pressurized air is conveyed from a conventional source of pressurized air common in dental offices, through the air supply line 60 coupled with the source of pressurized air by a coupling 70. The air supply line 60 is ultimately communicatively coupled with the air valve 47 and its respective reservoir head 34. Each air supply line 115 leads to the air inlet fitting 69 to supply pressurized air to the reservoir 30.

The pressurized air is supplied to force fluid 32 from the reservoir 30 through a distal end 40 of the fluid draw line 36 through the fluid outlet fitting 44 and through the fluid outlet lines 46, contained within an outlet line sheath 50, and ultimately to components of the handpiece 80.

With reference to FIG. 3, actuation of the air valve 47 may be accomplished by conventional means, supplied from an electrical power source 100 via power supply line 104, and controlled by means such as a programmable logic controller (PLC) 102. As further disclosed in FIG. 3, a single electrically operated air valve 47 receives pressurized air from the air supply line 62 passing through the adjustable air pressure regulator 64 a to a tee-fitting 74, where one port supplies air to an air line 114. The other port of the tee-fitting 74 being in communication with a pressure gauge 68. The pressurized air is delivered from the air valve 47 through hydrophobic filters 71 and to individual air inlet fittings 69 on the reservoir heads 34, thus pressurizing the fluid 32 and forcing the same through the fluid draw lines 36 to the fluid outlet lines 46 and through check valves 48. As will be described later, the fluid outlet lines 46 communicate with the handpiece 80. The hydrophobic filter 71, is disclosed schematically in FIG. 3, and a physical embodiment will be later shown and described.

As shown in FIG. 3, the present embodiment further contemplates the use of separate common tee-fittings 73 and 74. Here, the air supply line 62 enters the fluid supply system 10, and the air supply line 62 is split by a first common tee fitting 73 to split the air passage into two distinct pathways. One pathway 111 leads to the adjustable air pressure regulator 64 from the fixed air pressure regulator 65. Another pathway 112 for air travel leads to the fixed air pressure regulator 65. Preferably, the first common tee fitting 73 may be used to split the air flow into two distinct pathways.

Air enters the fixed air pressure regulator 65 through air supply line 62. Leaving the adjustable air pressure regulator 64, an air outlet line 67 is split by the second common tee-fitting 74 to split the air passage into two distinct pathways. As shown on FIG. 3, one pathway 113 leads to the pressure gauge 68. Another pathway 114 leads to the air valve 47.

If the first common tee fitting 73 is not utilized, two separate pressurized air supply lines could be used with one air line directed to the air valve 47 and the other pressurized air supply line directed to the air-only handpiece 120.

Referring to FIGS. 2 and 3, the fluid draw line 36 is coupled to the apertured fluid outlet fitting 44 located on the underside of reservoir head 34. The fluid draw line 36 is sized to extend from the top of the reservoir 30 to a point which is near the bottom of the reservoir, so that the fluid supply system 10 can operate until the reservoir 30 is nearly empty of fluid 32. The fluid outlet line 46 is communicatively coupled with the fluid outlet fitting 44 on the upper side of the reservoir head 34, extending the pathway for fluid 32 leaving the reservoir 30. The previously mentioned hydrophobic filter 71 is seated within a through bore communicating at the underside of reservoir head 34 as shown in FIG. 3.

Alternatively, the fluid draw line 36 and the fluid outlet line 46 could be integrated into a single line serving the same purpose of providing a conduit for fluid 32 to leave the reservoir 30 and retain pressure within the reservoir 30, if an air-tight fitting around the line is used as opposed to fluid outlet fitting 44. However, the use of both the fluid draw line 36 and the fluid outlet line 46 is preferred, mainly because this arrangement provides a better pressure seal than a single line with an air-tight fitting around the line. Each fluid outlet line 46 includes the check valve 48 coupled with the fluid outlet line 46, in order to prevent fluid 32 from flowing back into the reservoir 30.

A plurality of fluid outlet lines 46 emerge from the fluid supply system 10, (see FIG. 3) and enter a distal end of the outlet line sheath 50 (see FIGS. 1 and 2). The sheath 50 is preferably flexible, allowing ease of mobility during treatment of the patient, but also rigid enough to withstand penetration, line puncture, and kinking. The sheath 50 may be detachably coupled to a distal end of a handpiece handle 81 by a threaded couple, and the sheath 50 may be detachably coupled to a fluid reservoir manifold 39 by a similar threaded couple. After entering the distal end of the sheath 50, the fluid outlet lines 46 extend a predetermined distance from the distal end of the sheath and exit a proximal end of the sheath 50. The length of the sheath 50 and fluid outlet lines 46 is primarily determined by the distance between the fluid supply system 10 and the patient. Subsequently, the fluid outlet lines 46 enter a handpiece manifold 83 disposed within the handpiece handle 81, and the fluid outlet lines 46 are coupled with a plurality of respective fluid inlets 88 within the handpiece manifold 83. Also disposed within the handpiece handle 81 is a single fluid discharge line 52, through which a selected fluid passes into before being delivered into the patient's mouth.

Figure 7:
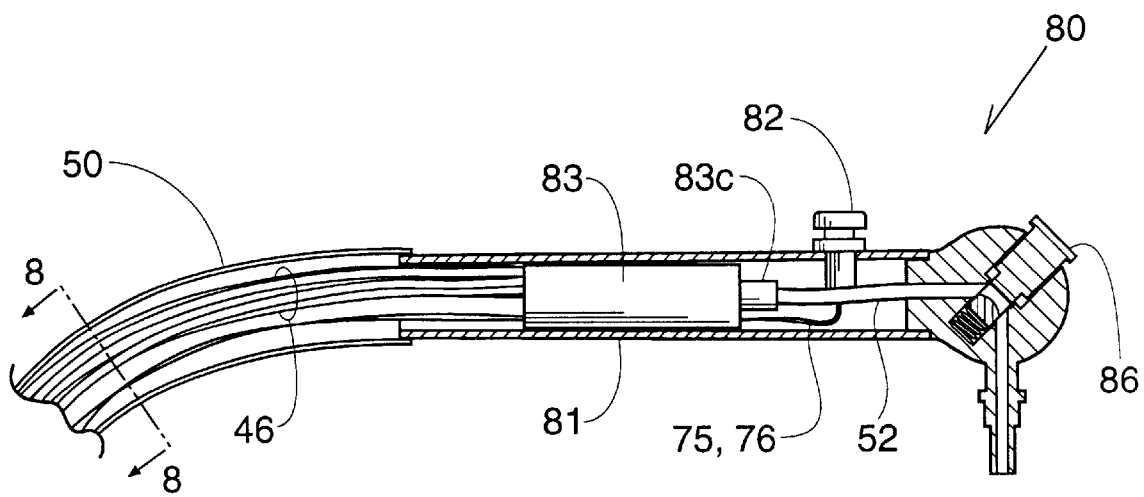
FIG. 7 is a longitudinal, sectional view of the handpiece of FIGS. 4–6, inclusive.
Figure 8:
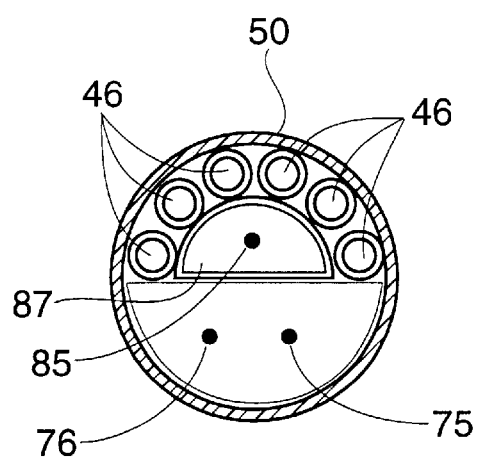
FIG. 8 is a cross-sectional view taken along lines 8—8 of FIG. 7.
Figure 9:
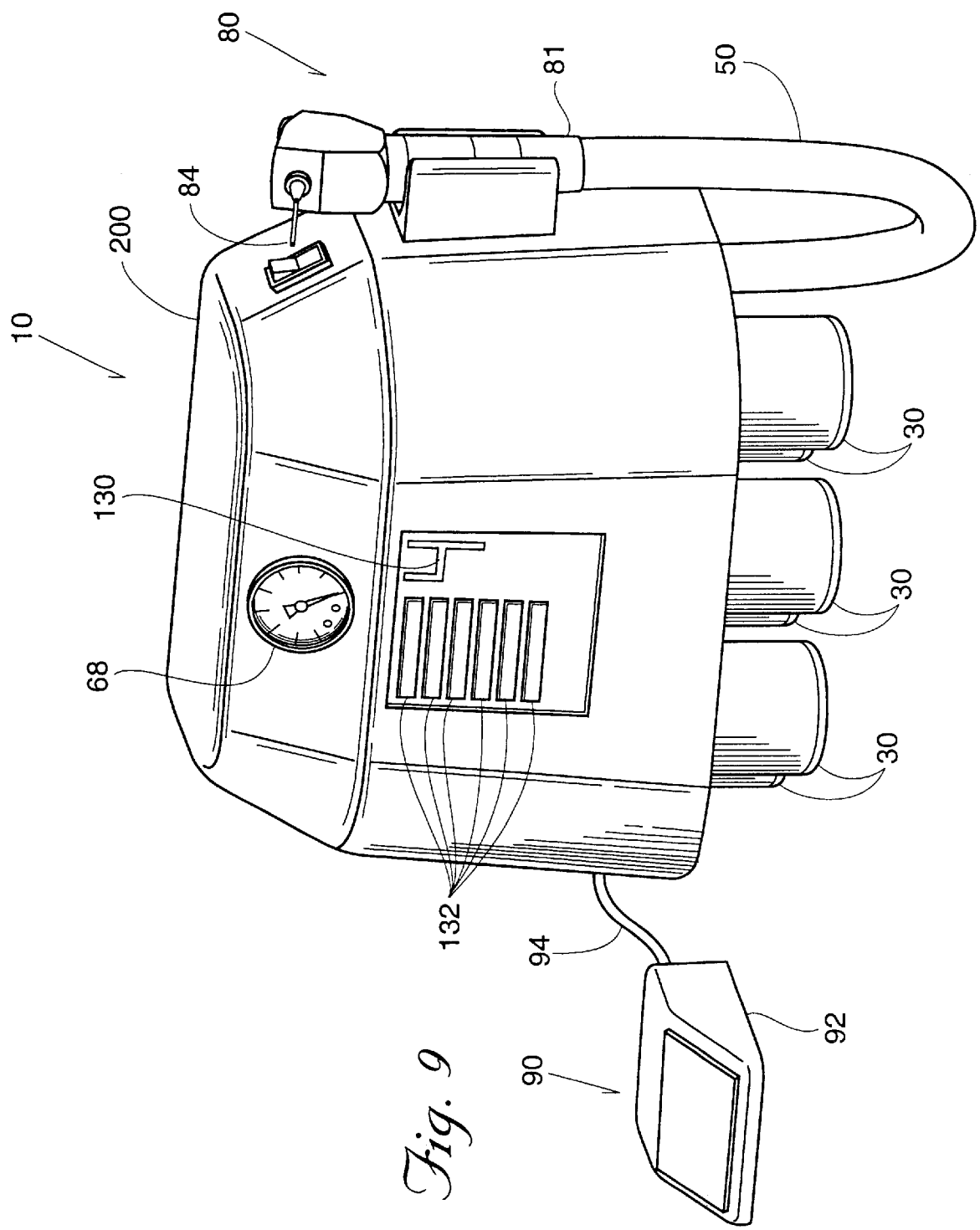
FIG. 9 is a perspective view of a modified fluid dispensing assembly, including a light emitting diode display and a touch pad assembly used in connection with the fluid dispensing assembly.
Figure 10:
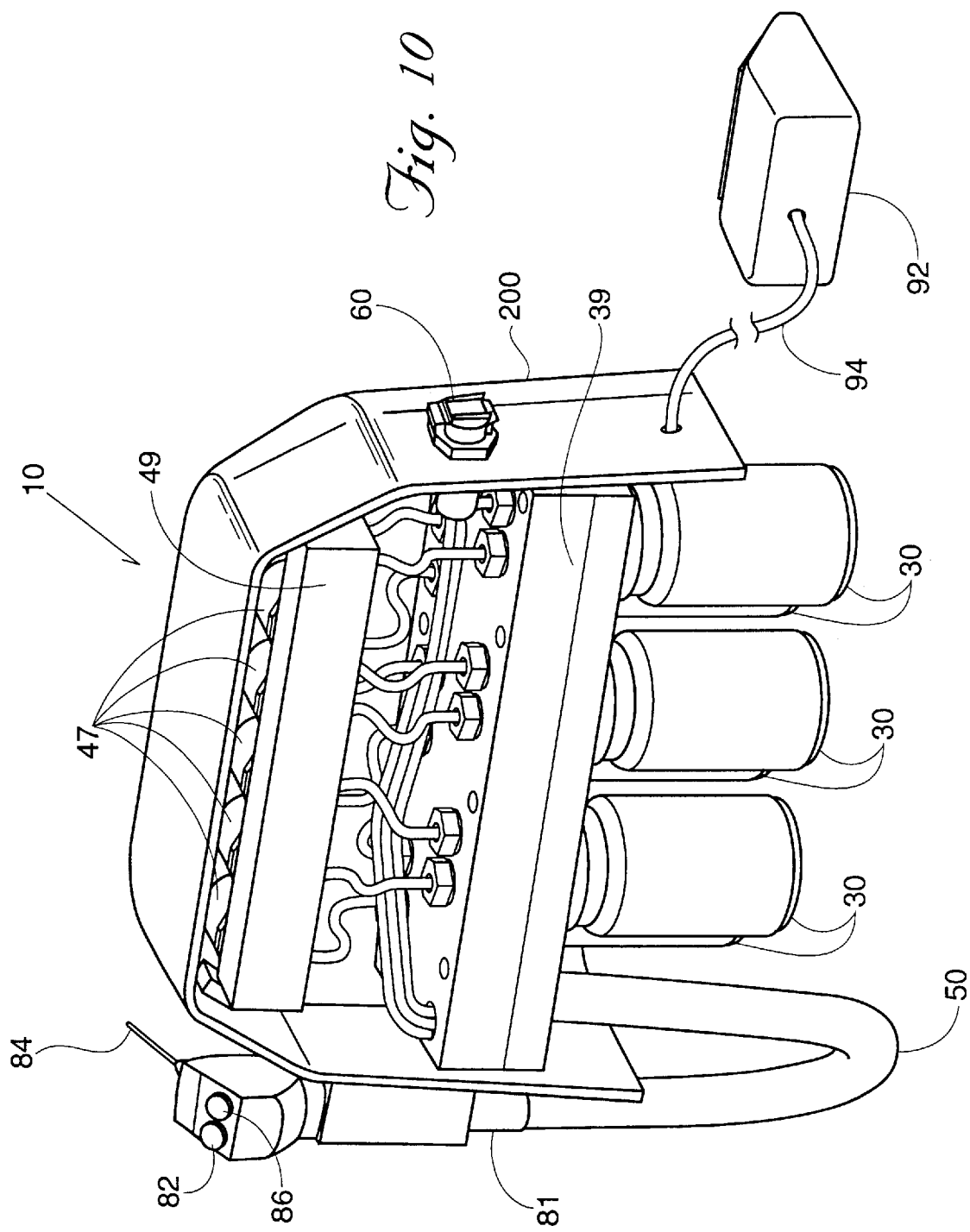
FIG. 10 is a rearward perspective view of the fluid dispensing assembly of FIG. 9.

In FIGS. 7 and 8, the cross-sectional view of FIG. 8 indicates the relationship of the fluid outlet lines 46 with respect to the sheath 50 and handpiece 80. As will be observed, it is preferable to arrange the fluid outlet lines 46 in a semi-circular pattern around a heating element 87, heated by at least one resistance wire 85 of substantially the same length as the fluid outlet lines 46. Thus, the fluid contained in the fluid outlet lines 46 will be pre-heated prior to discharge into the mouth of the patient, the temperature of said fluid being at a temperature that is suitable both for optimal patient comfort and for improving the efficacy of certain selected fluids with respect to the dental procedure being performed on the patient.

Referring to FIGS. 4–7, in order for the operator to select which fluid 32 to use, a momentary switch 82, such as a membrane switch, is provided on the handpiece 80. The switch 82 is connected to the PLC 102 by way of conductors 75, 76 as shown in FIGS. 3, 7 and 8. Pressure is delivered to the particular reservoir 30 containing the selected fluid 32, allowing the operator to quickly supply the desired fluid following a depression of the momentary switch 82, as opposed to having to wait for the air supply to re-pressurize the reservoir 30 with each alternation in fluid. In this arrangement, only one reservoir 30 is pressurized at a time.

Referring to FIGS. 1 and 2, the fluid supply system 10 is supplied with the housing 200, provided as a hub for simple instrumentation configuration changes, and as a hub for the fluid supply system 10 components. Carried by the housing 200 face is a light emitting diode display 130, which display utilizes a plurality of individual indicators 131. The individual indicators 131 indicate the particular fluid selected by the operator. The housing 200 creates an attractive portal for quick connections and flexibility during instrumentation, and also provides an easily accessible outside surface for regulating the air pressure with the air pressure regulator switch 66.

During instrumentation, an operator can configure the fluid supply system 10 to supply different fluids 32 and finger tip controlled irrigation, and aeration to a patient's mouth. Referring now to FIGS. 4–7, the dental handpiece 80 has a disposable tip 84, and the handpiece 80 may also have a disposable extension 79 for ease of accessing the patient's mouth. The extension 79 may be coupled to the handpiece 80 by a conventional LUER-LOK®-type fitting 78. The tip 84 receives the selected fluid 32 through the fluid discharge line 52 regulated by the pinch valve 86. The tip 84 is selectively coupled to the handpiece 80 and the tip 84 is then used during instrumentation to direct the deposit of fluids or evacuation target site in a patient's mouth. In this arrangement, only the relatively small amount of fluid 32 contained within the discharge line 52 and the tip 84 need be purged between fluid alternations.

Figure 22:
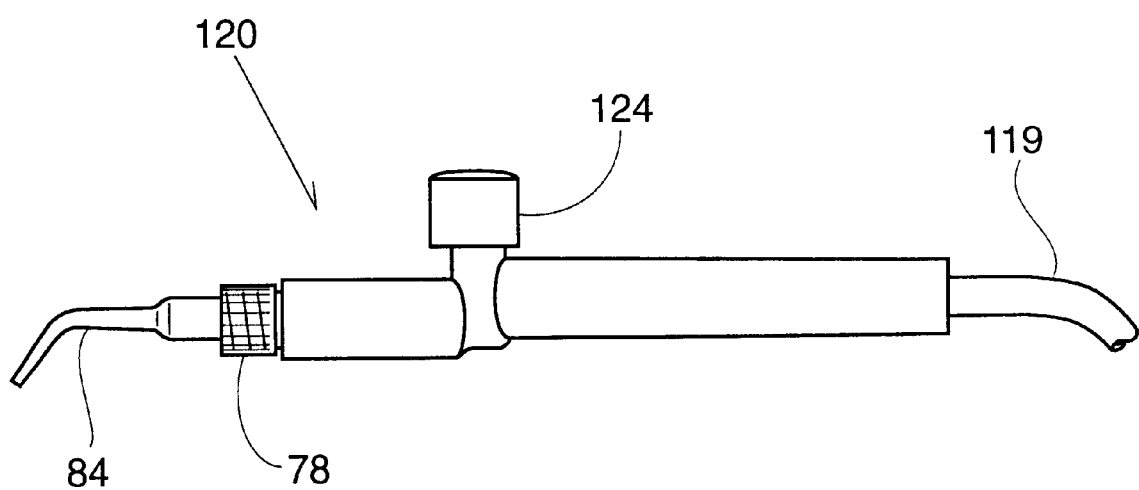
FIG. 22 is a side elevational view of an air-only handpiece of the present invention.

Referring to FIG. 2, if the operator desires to independently convey dry air to the patient's mouth, an air-only dental handpiece 120 is supplied. The air outlet line 119 is provided between the fluid supply system 10 and the air-only handpiece 120. Preferably, the air-only handpiece 120 is autoclavable, and has a tip 84, preferably disposable for use between different patients. The tip 84 receives the dry air through the air outlet line 119 coupled to the fixed air pressure regulator 65. The handpiece 120 is used during instrumentation to direct a stream of pressurized air in a patient's mouth. A control mechanism 124, in the form of a valve, may be disposed on the air-only handpiece 120 for actuating between air discharge and no discharge (see FIG. 22).

Figure 12:
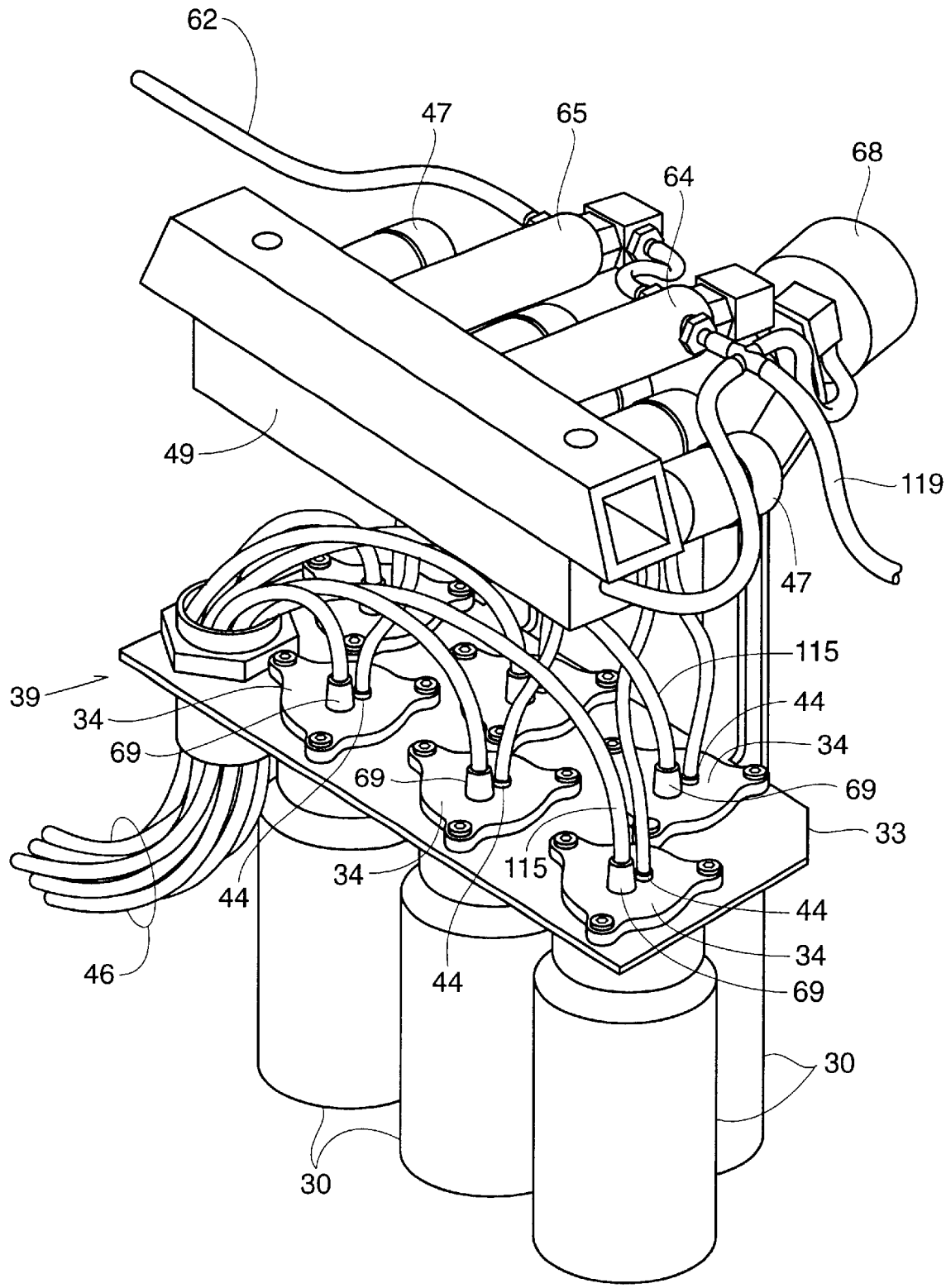
FIG. 12 is a rearward perspective view of the components of the fluid dispensing assembly with the housing removed.
Figure 13:
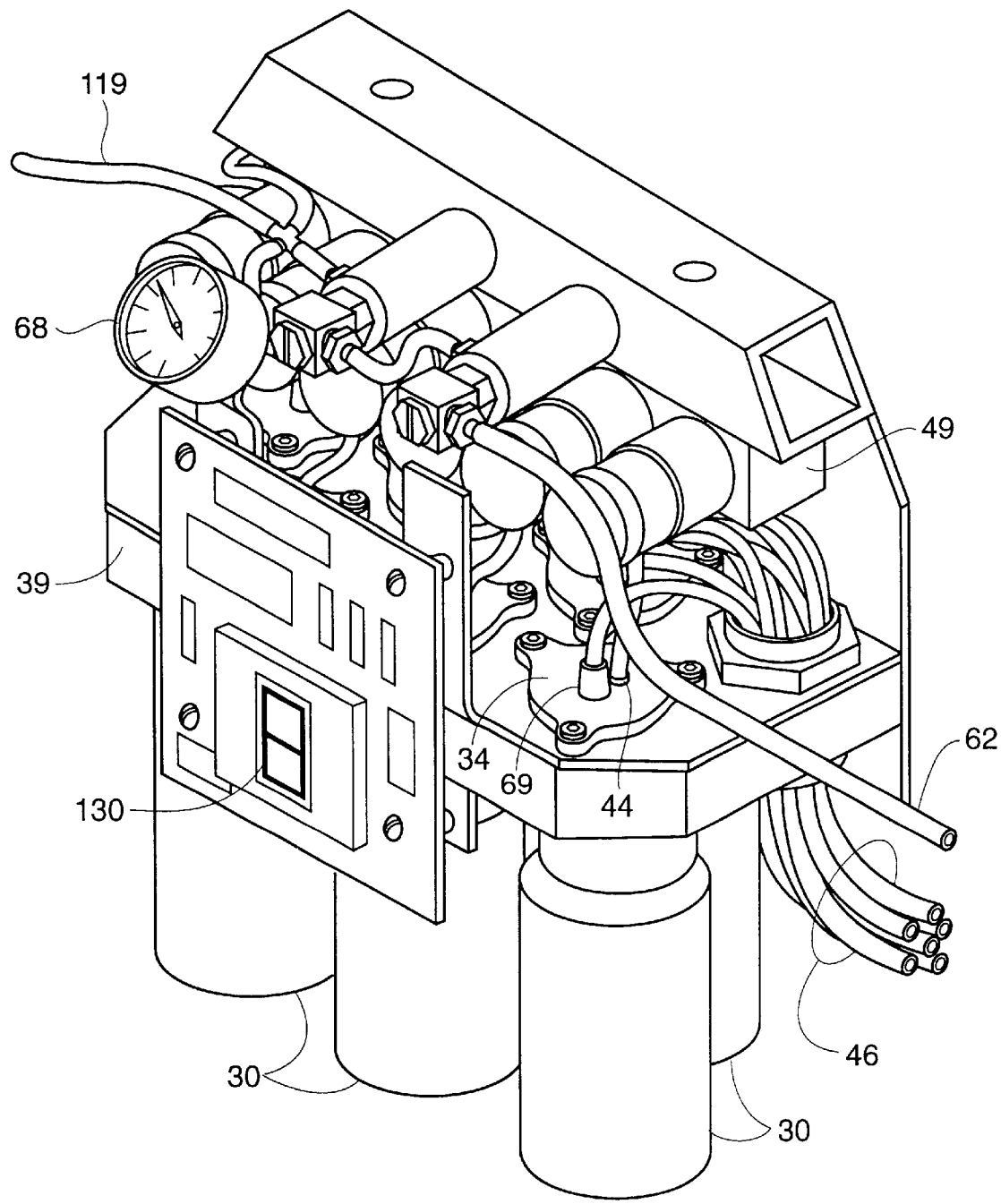
FIG. 13 is a frontal perspective view of the components of the fluid dispensing assembly with the housing removed.
Figure 14:
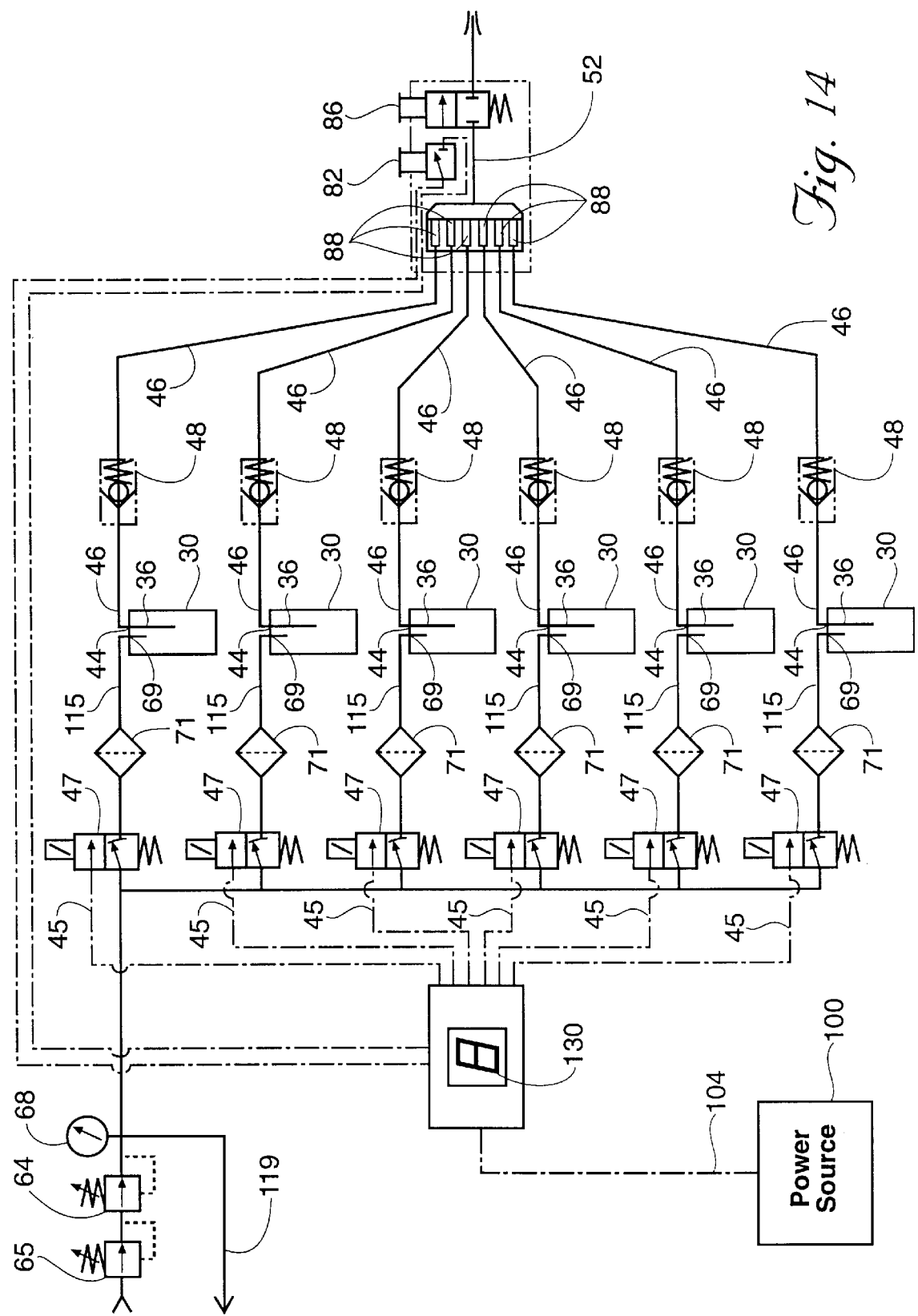
FIG. 14 is an alternate schematic view of the components of another embodiment of the fluid dispensing assembly of this invention.
Figure 15:
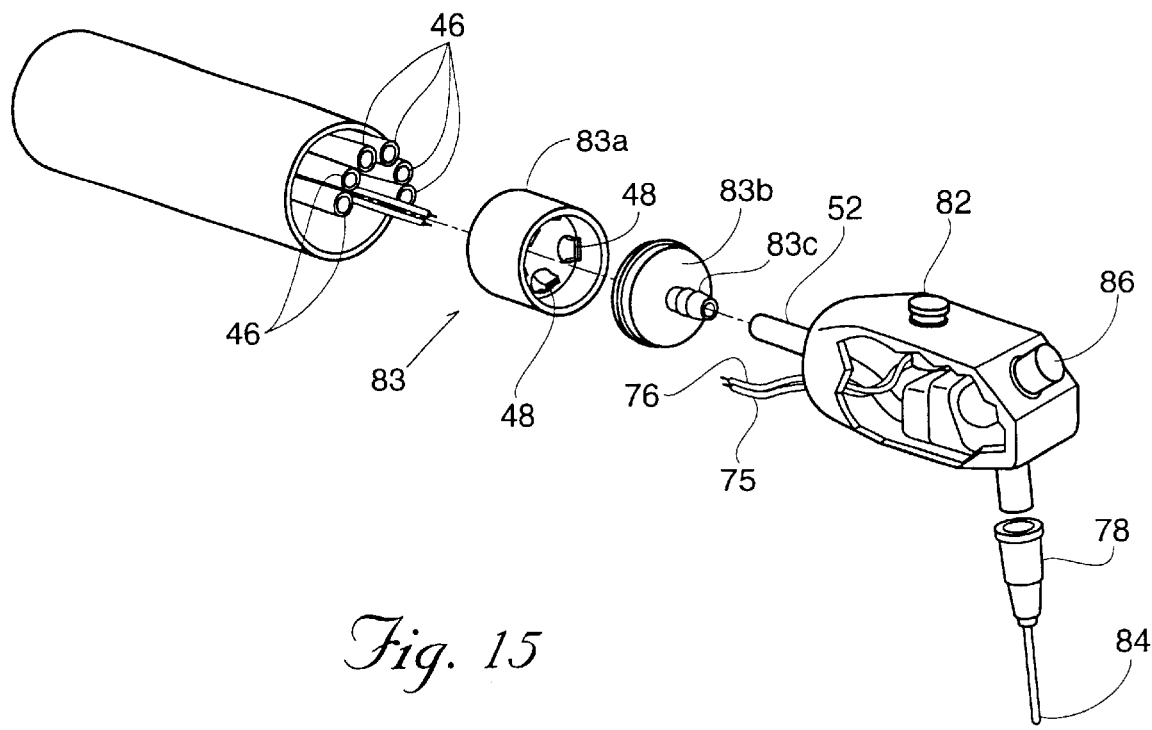
FIG. 15 is an exploded perspective view of a modified handpiece of the fluid dispensing assembly.
Figure 16:
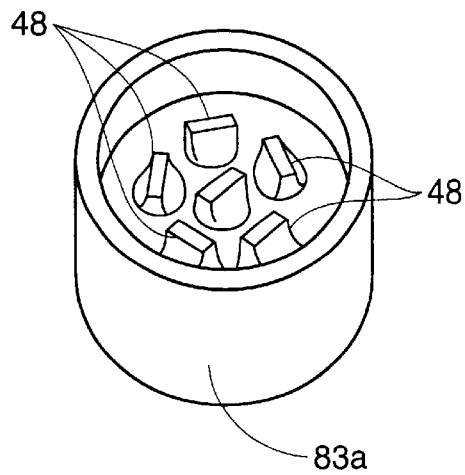
FIG. 16 is a perspective view of a portion of a manifold arranged to be located within the handpiece of the fluid dispensing assembly.

Now referring to FIGS. 12 through 14, in a preferred embodiment there are provided separate air valves 47. It is preferred to utilize conventional venting air valves because of the immediate release of pressure in the reservoir 30. However, simple two-way air valves may be substituted and the same result will be achieved. In this embodiment, after the air supply line 62 enters the fluid supply system 10 and passes through the fixed air pressure regulator 65 and through the adjustable air pressure regulator 64, the pressurized air is then split in three directions. The first directed path leads to the pressure gauge 68. The second directed path leads to the air-only handpiece 120. The third directed path leads to a valve manifold 49. The individual air valves 47 are each controlled by conventional logic circuitry supplying current to electric valve control lines 45, shown in phantom in FIG. 14. Hydrophobic filters 71 are also supplied in the schematic circuit as shown.

One hydrophobic filter that performs suitably is Model TA 65, available from PERFORMANCE SYSTEMATIX INC. of Caledonia, Mich., and which hydrophobic filter 71 consists of a hydrophobic membrane contained within a polyethylene frame. In the event the housing 200 is jostled or is tipped upside down, the hydrophobic filter 71 prevents fluid 32 from escaping the reservoir 30 and entering the air valve 47. Over time, an accumulation of the escaped fluid in the air valve 47 would lead to corrosion of the air valve 47 and subsequently to contamination of fluid 32 in the reservoir 30 when air is forced through a corroded air valve 47 and into the reservoir 30. Such an arrangement eliminates a threat of cross-contamination of fluid 32 in the reservoir 30.

As seen in FIGS. 15–19, inclusive, preferably the check valves 48 are preferably integrally molded in the handpiece manifold 83, comprising a cup—like base member 83a and an enclosure member 83b. The enclosure member 83b includes a fluid exit port provided by the bore of a barbed fitting 83c, for supplying the selected fluid to the patient's mouth through the fluid discharge line 52. The check valves 48 protrude from a base surface 89 to provide flexible, normally closed bill-like members, 48a and 48b. Silicone rubber is a suitable molding material to provide flexibility to oppositely disposed bill-like members 48a and 48b. Placement of the check valves 48 within the handpiece manifold 83 is preferred due to the ease of cleaning the component members of the handpiece manifold 83. Further, by placing the check valves 48 within the handpiece manifold 83, cross contamination of fluid 32 due to a backflow of fluid from the tip 84 is prevented.

Figure 17:
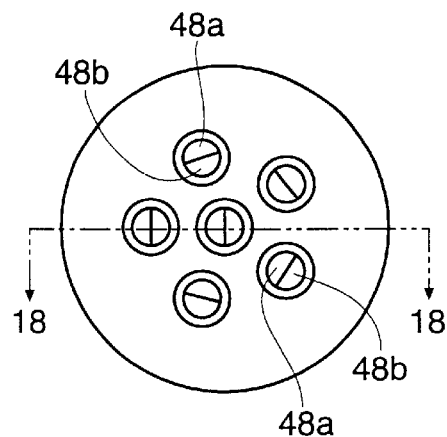
FIG. 17 is a top plan view of the manifold of FIG. 16, showing the normally closed position of individual check valves located in the manifold.
Figure 18:
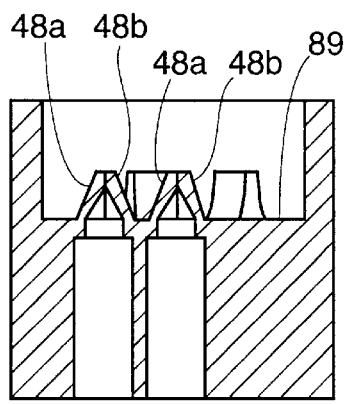
FIG. 18 is a longitudinal sectional view taken along lines 18—18 of FIG. 17.
Figure 19:
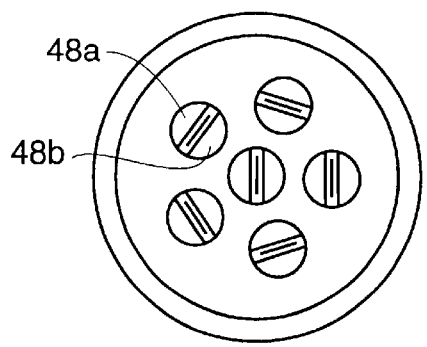
FIG. 19 is a top plan view similar to the view of FIG. 17, but showing the individual check valves in open operating position.
Figure 20:
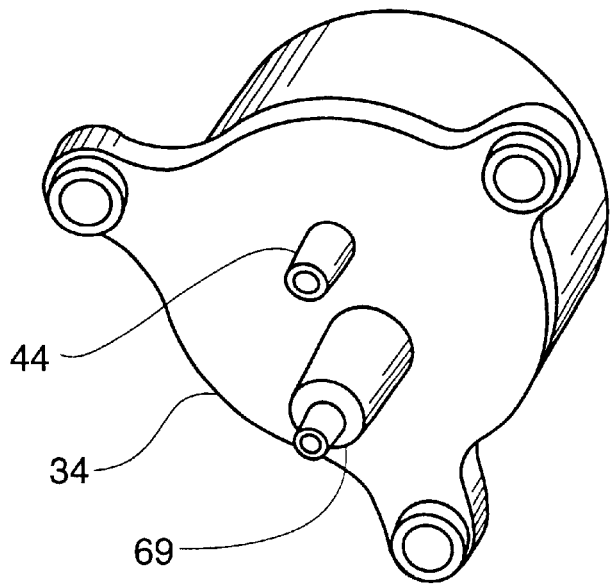
FIG. 20 is a top perspective view of a reservoir head.
Figure 21:
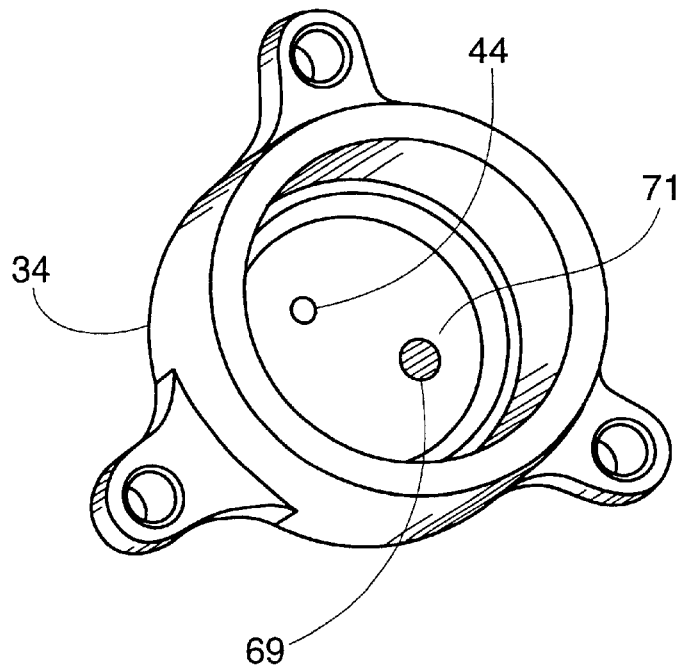
FIG. 21 is a bottom perspective view of the reservoir head of FIG. 20.

Pressurized fluid forces the normally closed bill—like members 48a and 48b, as shown in FIG. 17, to open the flexible bill—like members 48a and 48b to the position shown in FIG. 19. Closure of the pinch valve 86 will stop fluid flow and the members 48a and 48b will be permitted to close to the position shown in FIG. 17.

With reference to FIG. 12, it will be observed that the fluid reservoir manifold 39 comprises a plurality of reservoir heads 34 mounted on an apertured reservoir manifold plate 33. The heads 34 have been previously described to provide a detachable coupling for engaging the threaded neck 31 of each of the reservoirs 30.

In the preferred embodiment, the housing face 200 carries a light emitting diode display and a plurality of labels 132. Each label 132 is sequentially numbered and each label 132 corresponds to a different fluid 32 contained within a particular reservoir 30. When the operator selects a fluid 32 to use, the light emitting diode display 130 displays a number that corresponds to the selected fluid 32.

Figure 11:
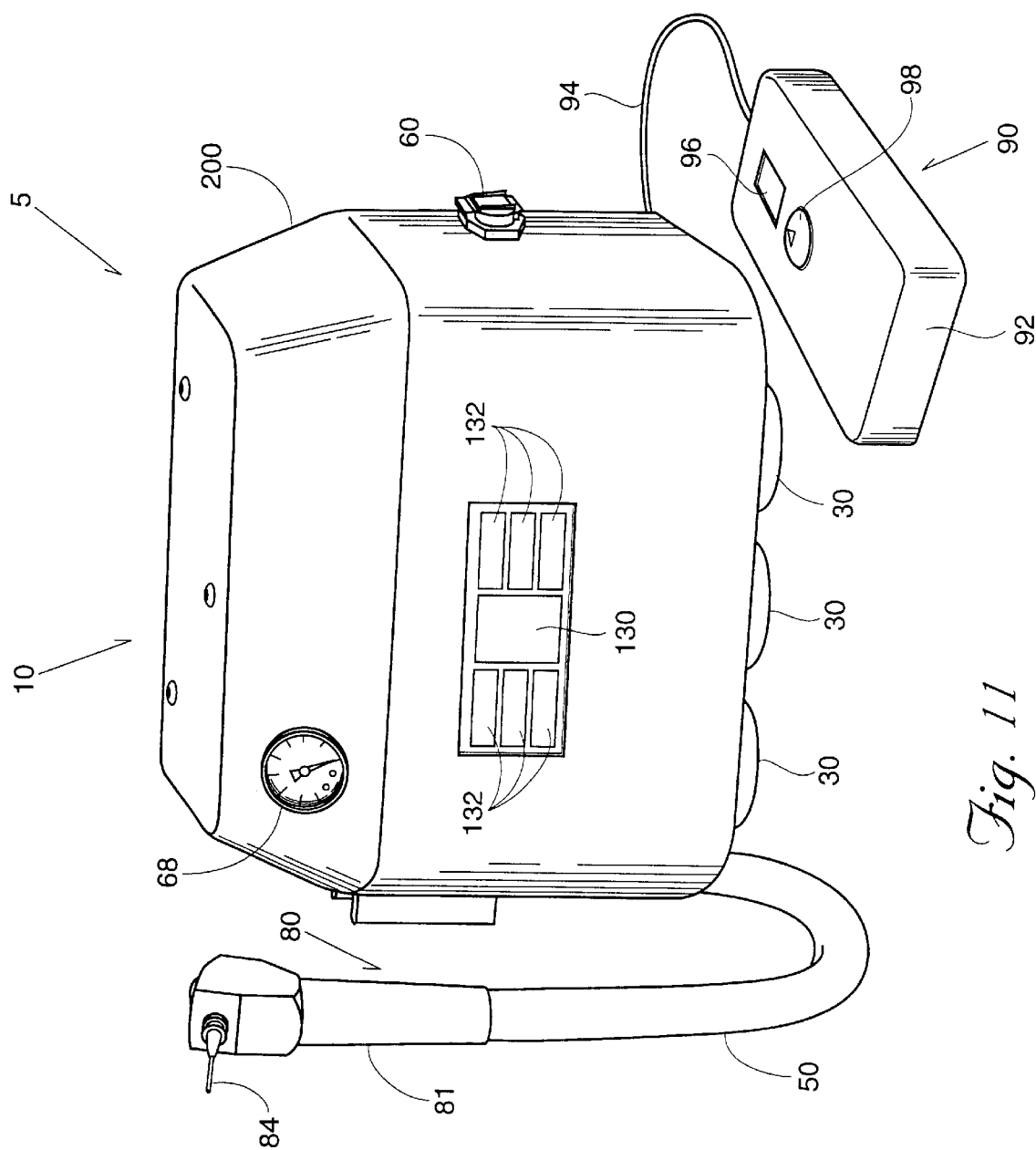
FIG. 11 is a perspective view of the modified fluid dispensing assembly, including an alternate display and touch pad assembly.

Referring now to FIG. 11, in one embodiment of the present invention, the fluid supply system 10 is equipped with a remote touch pad assembly 90. The touch pad assembly 90 includes a housing 92, a cord 94, a light emitting diode display 96, and a momentary switch 98. The touch pad assembly 90 is communicatively coupled to the fluid supply system 10 by the cord 94. If the touch pad assembly 90 is employed, the momentary switch 82 may not be disposed on the handpiece 80. The operator selects which fluid to use by depressing the momentary switch 98 on the touch pad assembly 90. The selected fluid is indicated by the light emitting diode display 96 on the face of the touch pad assembly 90 and/or the light emitting diode display 130 on the housing 200.

To supply a selected fluid 32 to the handpiece 80, the user first attaches the plurality of fluid-containing reservoirs 30 to the respective reservoir heads 34. Next, the user couples the plurality of fluid outlet lines 46 between the fluid containing reservoirs 32 and the handpiece 80. The user can then depress momentary switch 82 disposed on the handpiece 80 or momentary switch 98 disposed on the touch pad housing 92 in order to select the desired fluid. The momentary switch is operable to select a particular fluid 30 from among a plurality of fluids. After depressing the momentary switch, air pressure is supplied to the selected fluid-containing reservoir 30, and the pressurized air forces the fluid 32 from the selected fluid-containing reservoir 30 through the respective fluid outlet line 46 to the handpiece 80. Next, the user actuates the control mechanism 86 to allow the fluid 32 to pass from the selected fluid outlet line 46 through the handpiece 80 and ultimately the tip 84.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

What is claimed is:

1. A fluid dispensing assembly for dispensing a fluid selected from a plurality of fluid sources, the fluid dispensing assembly comprising:

a handpiece;

fluid discharge means disposed on the handpiece;

a handpiece manifold disposed within the handpiece;

said handpiece manifold including a plurality of fluid inlets and at least one fluid outlet;

a first control mechanism disposed on the handpiece, for controlling the amount of fluid flowing from said manifold fluid outlet to said fluid discharge means;

a second control mechanism disposed on the handpiece, said second control mechanism including an electrically operated selector circuit having momentary switching means for selecting a fluid from said plurality of fluids and for directing the selected fluid to one of said manifold fluid inlets.

2. A fluid dispensing assembly in accordance with claim 1, the fluid dispensing assembly further comprising:

a second handpiece for delivering only air;

an air-only discharge means disposed on the second handpiece; and a third control mechanism disposed on the second handpiece, for controlling the amount of air flowing through said second handpiece to said air-only discharge means.

3. A fluid dispensing assembly according to claim 1, wherein the fluid dispensing assembly further comprises:

a fluid supply system;

a housing for the fluid supply system; and a plurality of fluid outlet lines, the fluid outlet lines being communicatively coupled between the fluid supply system and the fluid inlets of said handpiece manifold.

4. A fluid dispensing assembly according to claim 3, wherein the fluid supply system comprises:

a plurality of fluid reservoirs;

a reservoir manifold arranged to detachably support said plurality of reservoirs;

a volume of fluid contained within each reservoir; and a plurality of reservoir heads, each head being coupled to the reservoir manifold and each head being adapted to detachably support and enclose a respective reservoir.

5. A fluid dispensing assembly according to claim 4, wherein the fluid outlet lines are communicatively coupled with the reservoir heads, and wherein the fluid supply system further comprises:

a fluid draw line contained within each reservoir, each fluid draw line being communicatively coupled with its respective reservoir head.

6. A fluid dispensing assembly according to claim 5, each fluid outlet line having a proximal end and a distal end, each fluid draw line having a proximal end and a distal end, the fluid supply system further comprising:

a fluid passage disposed through each reservoir head, the fluid passage having an interior end and an exterior end;

the proximal end of each of the fluid draw lines coupled with the interior end of one of the fluid passages, the proximal end of each of the fluid outlet lines coupled with the exterior end of one of the fluid passages, the distal end of each of the fluid outlet lines coupled to one of the handpiece manifold fluid inlets.

7. A fluid dispensing assembly according to claim 6, wherein the fluid supply system further comprises:
a check valve coupled with at least one fluid outlet line.

8. A check valve according to claim 7, wherein a respective one of a plurality of said check valves is located within said handpiece manifold and said check valve is in communication with a respective handpiece manifold fluid inlet.

9. The fluid dispensing assembly in accordance with claim 7, wherein said check valve is formed integrally within the handpiece manifold.

10. The fluid dispensing assembly according to claim 7, wherein said check valve comprises oppositely disposed, flexible bill-like members in a normally closed relationship, and when said bill-like members are opened under fluid pressure, fluid is permitted to pass therethrough to said fluid discharge means, and when said flexible bill-like members are permitted to return to normally closed relationship, said check valve will block fluid back flow from the fluid discharge means into the fluid supply system.

11. A fluid dispensing assembly according to claim 4, wherein the fluid supply system further comprises:
a source of pressurized air; and
an air supply line communicatively coupled between the source of pressurized air and each reservoir head, the pressurized air being at a pressure capable of forcing fluid from each reservoir to a respective one of the fluid inlets of the handpiece manifold.

12. A fluid dispensing assembly according to claim 11, wherein the fluid supply system further comprises:
air pressure regulating means coupled with the air supply line, said means being disposed between the source of pressurized air and each reservoir head.

13. A fluid dispensing assembly according to claim 11, wherein the fluid supply system additionally comprises:
air pressure regulating means coupled with the air supply line, said means being disposed between the source of pressurized air and each reservoir head; and
a common tee fitting including an air inlet port and first and second outlet ports, said first outlet port being in communication with said air pressure regulating means and said second outlet port being in communication with a second handpiece for delivering only air.

14. A fluid dispensing assembly according to claim 13, wherein the air pressure regulating means includes an adjustable air pressure regulator.

15. A fluid dispensing assembly according to claim 13, wherein the air pressure regulating means includes a fixed air pressure regulator.

16. A fluid dispensing assembly according to claim 13, wherein the air pressure regulating means includes both a fixed air pressure regulator and an adjustable air pressure regulator.

17. A fluid dispensing assembly in accordance with claim 11, wherein the fluid supply system further comprises:
electrically operated valve means located between the source of pressurized air and the reservoir; and
said electrically operated valve means being controlled by the electrically operated selector circuit.

18. The fluid dispensing assembly in accordance with claim 17, wherein the electrically operated selector circuit includes a programmable logic controller.

19. A fluid dispensing assembly in accordance with claim 17, wherein said electrically operated valve means includes a valve manifold;
said valve manifold adapted to support and retain a plurality of said electrically operated valves, a respective one of said plurality of electrically operated valves being in fluid communication with a selected one of said reservoirs.

20. A fluid dispensing assembly in accordance with claim 19, wherein said electrically operated valve means comprises a single electrically operated valve controlled by the electrically operated selector circuit; and
wherein said electrically operated valve includes a plurality of fluid outlet ports, each of said ports being in fluid communication with a selected one of said reservoirs.

21. A fluid dispensing assembly according to claim 20, wherein the fluid supply system additionally comprises:
air pressure regulating means coupled with the air supply line, said means being disposed between the source of pressurized air and each reservoir head;
a first common tee fitting including an air inlet port and first and second outlet ports, said first outlet port being in communication with said air pressure regulating means and said second outlet port being in communication with a second handpiece for delivering only air;
an air pressure gauge;
a second common tee fitting including an air inlet port and first and second outlet ports, said air inlet port being in communication with said air pressure regulating means; and
said first air outlet port being in communication with said air pressure gauge; and said second air outlet port being in communication with said single electrically operated valve.

22. A fluid dispensing assembly in accordance with claim 11, wherein the fluid supply system further comprises a hydrophobic air filter located between the source of pressurized air and the reservoir head.

23. A fluid dispensing assembly in accordance with claim 22, wherein said hydrophobic air filter is disposed within each reservoir head.

24. A fluid dispensing assembly in accordance with claim 4, wherein the fluid supply system further includes a light emitting diode display for indication of the fluid flow from a selected reservoir.

25. A fluid dispensing assembly according to claim 3, wherein the fluid supply system further comprises fluid heating means.

26. The fluid heating means of claim 25, said fluid heating means being arranged proximate to at least a portion of said fluid outlet lines, and being further adapted to warm a fluid being transported through a respective fluid outlet.

27. A fluid dispensing assembly according to claim 3, wherein the momentary switching means is disposed on the first handpiece, and said momentary switching means being communicatively coupled to the fluid supply system.

28. A fluid dispensing assembly according to claim 3, wherein the momentary switching means is disposed on a remote touch pad, said remote touch pad switching means being communicatively coupled to the fluid supply system.

29. A fluid dispensing assembly according to claim 3, wherein the momentary switching means is disposed both on the first handpiece and on a remote touch pad, said momentary switching means being communicatively coupled to the fluid supply system.

* * * * *

UNITED STATES PATENT AND TRADEMARK OFFICE
CERTIFICATE OF CORRECTION

PATENT NO. : 6,390,815 B1
DATED : May 21, 2002
INVENTOR(S) : Gary J. Pond

It is certified that error appears in the above-identified patent and that said Letters Patent is hereby corrected as shown below:

<u>Title page,</u>
Item [56], Refernces Cited, FOREIGN PATENT DOCUMENTS, insert
-- 4,797,098, 01/1989, Kawata --.

Signed and Sealed this

Eighth Day of June, 2004

JON W. DUDAS
*Acting Director of the United States Patent and Trademark Office*